(12) United States Patent
Liang et al.

(10) Patent No.: US 11,739,067 B2
(45) Date of Patent: Aug. 29, 2023

(54) SUPER-HYDROPHOBIC ELECTROTHERMAL EPOXY RESIN COMPOSITE MATERIAL AND PREPARATION AND SELF-REPAIRING METHOD THEREFOR

(71) Applicant: SOOCHOW UNIVERSITY, Suzhou (CN)

(72) Inventors: Guozheng Liang, Suzhou (CN); Youhao Zhang, Suzhou (CN); Aijuan Gu, Suzhou (CN); Li Yuan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 627 days.

(21) Appl. No.: 17/003,569

(22) Filed: Aug. 26, 2020

(65) Prior Publication Data
US 2020/0392299 A1     Dec. 17, 2020

Related U.S. Application Data

(63) Continuation of application No. PCT/CN2018/077460, filed on Feb. 27, 2018.

(51) Int. Cl.
*C07D 327/00* (2006.01)
*C08J 7/04* (2020.01)

(52) U.S. Cl.
CPC .......... *C07D 327/00* (2013.01); *C08J 7/0423* (2020.01); *C08J 2363/00* (2013.01)

(58) Field of Classification Search
None
See application file for complete search history.

(56) References Cited

U.S. PATENT DOCUMENTS

2006/0166003 A1* 7/2006 Khabashesku ...... D06M 13/196
                                                                 428/408
2014/0349061 A1* 11/2014 Sikka .................. B29C 37/0032
                                                                 428/98

FOREIGN PATENT DOCUMENTS

CN     102311713 A     1/2012
CN     104830031 A     8/2015
(Continued)

*Primary Examiner* — Joel G Horning
(74) *Attorney, Agent, or Firm* — SZDC LAW P.C.

(57) ABSTRACT

Superhydrophobic electrothermal epoxy composites, their preparation and a self-healing method are disclosed. 1,4,5-oxadithiepane-2,7-dione and methylhexahydrophthalic anhydride were mixed and cured with epoxides to get self-healable epoxy resins; carbon nanotube/self-healable epoxy resin prepolymers were coated on self-healable epoxy resins and cured to get electrothermal epoxy composites; modified superhydrophobic copper powders were adhered on electrothermal epoxy composites and cured to get a kind of superhydrophobic electrothermal epoxy composites. The thermal resistance of superhydrophobic electrothermal epoxy composites is superior to existed technical solutions and they can simultaneously repair cracking and delamination and the healed samples still exhibit excellent superhydrophobicity. These merits of superhydrophobic electrothermal epoxy composites provided in this invention can meet the harsh requirements of self-healing and removing ice on surfaces of wind turbine blades, suggesting good abilities of guaranteeing service safety and lifespan of wind turbine blades.

8 Claims, 6 Drawing Sheets

(56) References Cited

FOREIGN PATENT DOCUMENTS

| | | |
|---|---|---|
| CN | 107418147 A | 12/2017 |
| CN | 108530661 A | 9/2018 |

\* cited by examiner

SUPER-HYDROPHOBIC ELECTROTHERMAL EPOXY RESIN COMPOSITE MATERIAL AND PREPARATION AND SELF-REPAIRING METHOD THEREFOR

This application is a Continuation Application of PCT/CN2018/077460, filed Feb. 27, 2018, which is which is incorporated by reference for all purposes as if fully set forth herein.

TECHNICAL FIELD

This invention relates to polymeric composites, their preparation and a self-healing method. More specifically, the invention relates to superhydrophobic electrothermal epoxy composites, their preparation and a self-healing method. It relates to the technical field of polymer materials.

BACKGROUND TECHNIQUE

Energy safety and environmental protection have become two major issues of global concern in the 21$^{st}$ century. Wind energy is one of the most important renewable sources, and wind turbine generators have been widely promoted in Asia, Europe, Oceania and America. Surface icing is one of the main threats to the maintenance of wind turbine blades that are applied in high altitude regions or clammy and freezing environments. The balance and weight of wind turbine blades will be affected by surface icing, which not only causes deformation of blades, but also reduces the efficiency of generating electricity, and thus shortening the lifespan of wind turbines. Therefore, it is of great importance to develop ice-removing techniques for wind turbine blades to ensure their secure and stable utilization in high altitude regions or clammy and freezing environment. At present, hydrophobic coatings and electrothermal coatings based on polymeric composites are two primary strategies provided by most manufacturers to remove ice. Through the combination of these two functional coatings, ice is firstly melt by absorbing the heat transformed from electricity, and then the ice-water mixture rolls off the surface of blades due to the hydrophobic surface coating of blades; consequently, the aim of ice-removing is implemented.

Obviously, the variable climate has strictly asked for better reliability of epoxy resins and its derivative functional composites used in wind turbine blades. In recent years, intrinsic self-healable materials have attracted worldwide attention because they can repeatedly repair physical damages and flaws, prevent materials from failure and extend the service life.

However, the introduction of intrinsic self-healing ability to the design of wind turbine blades still has some barriers to overcome. Firstly, to get self-healing ability at moderate temperature, most self-healable epoxy resins reported have low glass transition temperature values ($T_g$<70° C.) and initial decomposition temperature ($T_{di}$, <300° C.). Although the relatively low $T_g$ is beneficial to realize self-healing ability at certain temperature (from R.T. to 200° C.), they do not meet the requirement on high glass transition temperature (>70° C.) for fabricating wind turbine blades and bearing the high ice-removing temperature (60~80° C.).

Secondly, $T_g$ values of previously reported self-healable conductive and electrothermal coatings fall in the range from −120 to 20° C., which are much lower than the ice-removing temperature (60~80° C.) of wind turbine blades at work. Once the ice-removing temperature is higher than $T_g$, the electrothermal coating enters into rubbery state, and then deformation is much likely to take place under the effect of gravity. What's more, for present superhydrophobic coatings, their healing behaviors are derived from two mechanisms; one is the migration and rearrangement of polymers with low surface energy (such as long-chain alkanes, polyfluorinates compounds and polydimethylsiloxanes) grafted on the surface of coatings, the other is controlled release and delivery of above polymers with low surface energy from inserted micro-containers within coatings. Note that these two mechanisms establish under the promise of maintaining perfect hierarchical micro-nano structures, so slight friction or oxidation can be healed, but the failure of superhydrophobicity caused by abrasion and fracture cannot be healed.

Therefore, it is still an interesting issue with great challenge to develop novel multi-layered superhydrophobic electrothermal epoxy composites with superior self-healing ability and high thermal resistance to repair cracking and delamination of wind turbine blades and guarantee ice-removing ability.

SUMMARY OF INVENTION

In order to achieve above purpose, the technical solution adopted by this invention is providing the preparation method of a kind of superhydrophobic electrothermal epoxy composites, which is composed of following steps:
  (1) By mass, at 50 to 70° C., 100 parts of epoxy resin, 42 to 84 parts of 1,4,5-oxadithiepane-2,7-dione and 0 to 43 parts of methylhexahydrophthalic anhydride were mixed homogeneously. After curing, a kind of self-healable epoxy resins was obtained.
  (2) By mass, at 50 to 70° C., 10 parts of epoxy resin, 4.2 to 8.4 parts of 1,4,5-oxadithiepane-2,7-dione and 0 to 4.3 parts of methylhexahydrophthalic anhydride were mixed homogeneously to get prepolymer; ester solvent and 0.1 to 4 parts of carbon nanotube were added to the prepolymer and mixed homogeneously to get a paste; the paste was coated on self-healable epoxy resins described in Step (1). After vaporizing ester solvent and curing, a kind of electrothermal epoxy composites was obtained.
  (3) By mass, 4 parts of copper nanopowders and 0.1 to 2 parts of perfluorocarboxylic acid were dispersed in water and mixed homogeneously. After filtration and drying, modified superhydrophobic copper powders were obtained.
  (4) By mass, at 50 to 70° C., 10 parts of epoxy resin, 4.2 to 8.4 parts of 1,4,5-oxadithiepane-2,7-dione and 0 to 4.3 parts of methylhexahydrophthalic anhydride were mixed homogeneously to get prepolymer; the prepolymer and modified superhydrophobic copper powders were successively dispersed on electrothermal epoxy composites described in Step (2). After curing, a kind of superhydrophobic electrothermal epoxy composites was obtained.

This invention provided the preparation method of a kind of electrothermal epoxy composites, which was composed of following steps:
  (1) By mass, at 50 to 70° C., 100 parts of epoxy resin, 42 to 84 parts of 1,4,5-oxadithiepane-2,7-dione and 0 to 43 parts of methylhexahydrophthalic anhydride were mixed homogeneously. After curing, a kind of self-healable epoxy resins was obtained.
  (2) By mass, at 50 to 70° C., 10 parts of epoxy resin, 4.2 to 8.4 parts of 1,4,5-oxadithiepane-2,7-dione and 0 to 4.3 parts of methylhexahydrophthalic anhydride were mixed homogeneously to get prepolymer; ester solvent and 0.1 to 4 parts of carbon nanotube were added to the prepolymer and mixed homogeneously to get a paste; the paste was coated on self-healable epoxy resins described in Step (1). After vaporizing ester solvent and curing, a kind of electrothermal epoxy composites was obtained.

The preferred preparation method of above-mentioned 1,4,5-oxadithiepane-2,7-dione is composed of following steps:

(1) By mass, at 20 to 30° C., 120 parts of 2-mercaptoacetic acid, 500 to 700 parts of ester solvent and 0.6 to 1.2 parts of potassium iodide were mixed homogeneously to obtain a solution; 80 to 90 parts of 30 wt % $H_2O_2$ were added dropwise to the solution and continued to react for 2 to 4 h to get 2,2'-dithiodiacetic acid.

(2) By mass, at 20 to 30° C., 100 parts of 2,2'-dithiodiacetic acid and 120 to 150 parts of anhydride were mixed homogeneously and continued to react for 2 to 4 h to get 1,4,5-oxadithiepane-2,7-dione.

The ester solvent described in above-mentioned technical solution is methyl acetate, ethyl acetate, propyl acetate, methyl propionate, ethyl propionate, or any combination thereof.

The perfluorocarboxylic acid described in above-mentioned technical solution is perfluorooctanoic acid, perfluorononanoic acid, perfluorodecanoic acid, or any combination thereof.

The epoxy resin described in above-mentioned technical solution is glycidyl ether type epoxy resin, glycidyl ester type epoxy resin, glycidyl amine type epoxy resin, aliphatic epoxides, alicyclic epoxides, or any combination thereof. The carbon nanotube described in above-mentioned technical solution is unprocessed single-walled carbon nanotube, multi-walled carbon nanotube, or any combination thereof.

The anhydride described in above-mentioned technical solution is acetic anhydride, trifluoroacetic anhydride, or any combination thereof.

The superhydrophobic electrothermal epoxy composites prepared by the above-mentioned preparation method. The electrothermal epoxy composites prepared by the above-mentioned preparation method.

This invention provides the application of 1,4,5-oxadithiepane-2,7-dione in preparation of above-mentioned superhydrophobic electrothermal epoxy composites or electrothermal epoxy composites.

The invention provides the self-healing method of superhydrophobic electrothermal epoxy composites, which is composed of following steps: fractured surfaces of damaged superhydrophobic electrothermal epoxy composites were brought into contact, held tightly by clamps and maintained at 160 to 200° C. for 1 to 3 h to fulfill their self-healing process.

The invention provides the self-healing method of electrothermal epoxy composites, which is composed of following steps: fractured surfaces of damaged electrothermal epoxy composites were brought into contact, held tightly by clamps and maintained at 160 to 200° C. for 1 to 3 h to fulfill their self-healing process.

Advantageous Effects of the Invention

The thermal resistance ($T_g$=113° C.) of superhydrophobic electrothermal epoxy composites provided in this invention is superior to existed technical solutions owing to the inherently high stiffness and crosslinking density of epoxy resins, and they can simultaneously self-repair cracking and delamination. The self-healing behavior of the superhydrophobic electrothermal epoxy composites is based on topology rearrangement of resin layers containing dynamic disulfide bonds and the healed samples still exhibit excellent superhydrophobicity by self-healing process of cracking and delamination from bottom resin layer to top superhydrophobic layer. The superhydrophobic electrothermal epoxy composites provided in this invention can meet the harsh requirements of self-healing and ice-removing on surfaces of wind turbine blades, suggesting good abilities of guaranteeing service safety and lifespan of wind turbine blades.

EXAMPLES OF THIS INVENTION

Example 1

1) Synthesis of 1,4,5-oxadithiepane-2,7-dione

Figure 1:
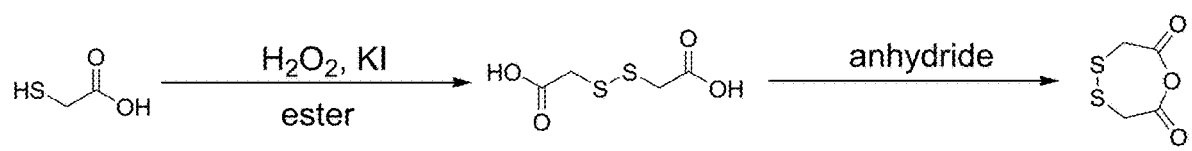
FIG. 1 is synthetic route of 1,4,5-oxadithiepane-2,7-dione synthesized in Example 1 of this invention.
Figure 2:
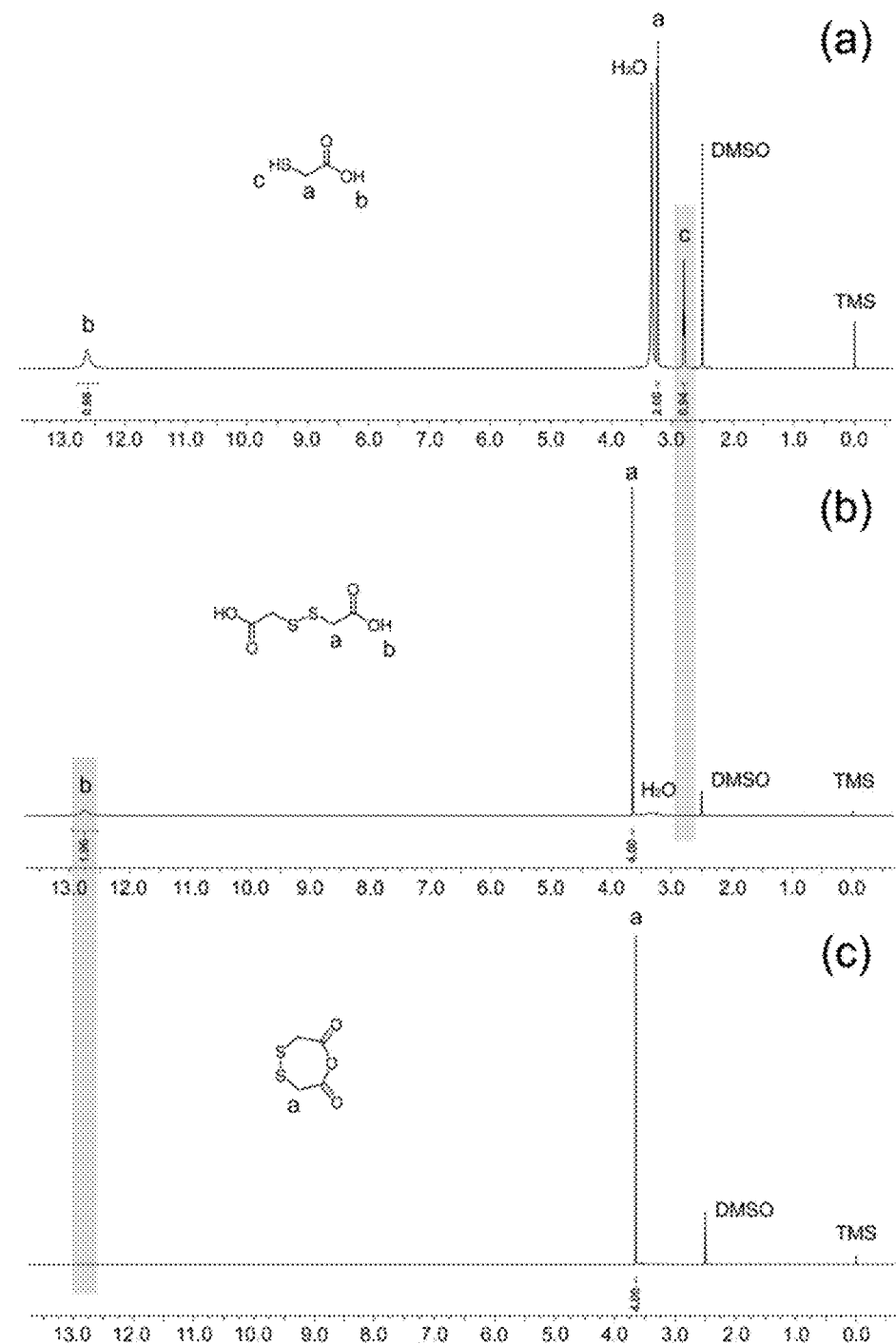
FIG. 2 is $^1$H-NMR spectra of the production of Example 1.

According to the synthetic route described in FIG. 1, the specific preparation method is composed of following steps: by mass, at 20° C., 120 g 2-mercaptoacetic acid, 500 g ethyl acetate and 0.6 g potassium iodide were mixed homogeneously to obtain a solution A; 80 g 30 wt % $H_2O_2$ were added dropwise to solution A and continued to react for 2 h. The obtained solution was washed with 300 mL saturate $Na_2SO_3$ aqueous solution and ethyl acetate was removed under reduced pressure to get 2,2'-dithiodiacetic acid. The $^1$H-NMR spectrum of 2,2'-dithiodiacetic acid is shown in FIG. 2.

By mass, at 20° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione. The $^1$H-NMR spectrum of 1,4,5-oxadithiepane-2,7-dione are shown in FIG. 2.

2) Synthesis of Self-Healable Epoxy Resins

Figure 3:
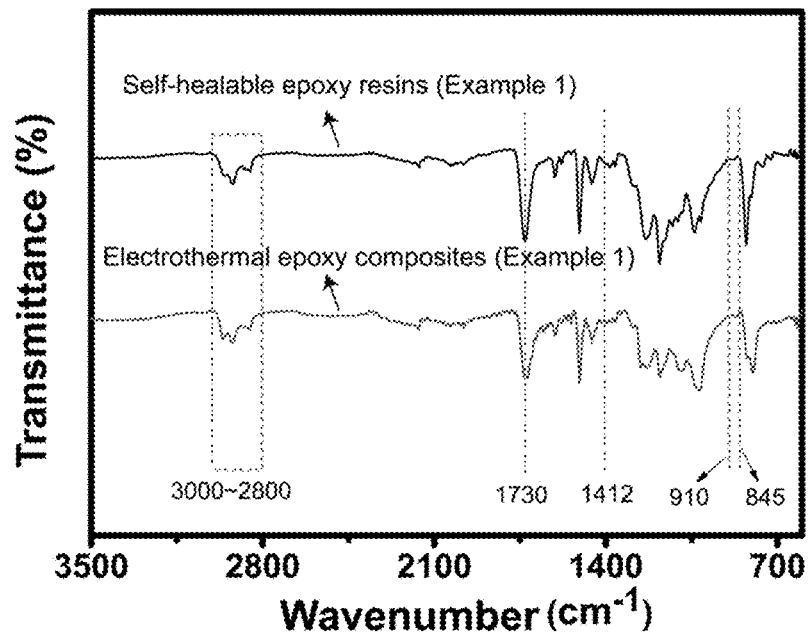
FIG. 3 is FTIR spectra of self-healable epoxy resin and electrothermal epoxy composite synthesized in Example 1 of this invention.
Figure 4:
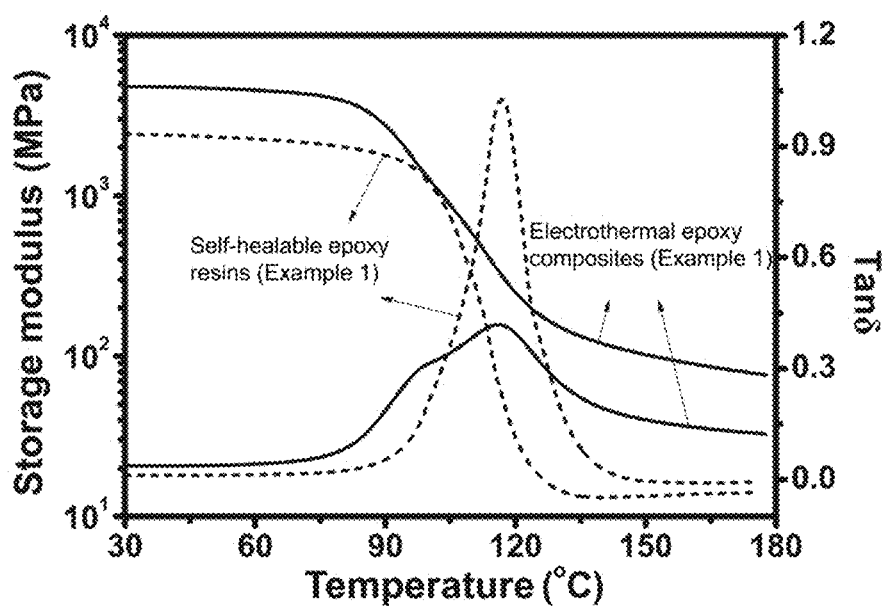
FIG. 4 is DMA curves of self-healable epoxy resin and electrothermal epoxy composite synthesized in Example 1 of this invention.

By mass, at 50° C., 100 g glycidyl ether type epoxy resin (E51, epoxide equivalent weight of 196 g/eq), 42 g of 1,4,5-oxadithiepane-2,7-dione, 43 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained. The FTIR spectrum and DMA curves of self-healable epoxy resins are shown in FIG. 3 and FIG. 4.

3) Synthesis of Electrothermal Epoxy Composites

Figure 5:
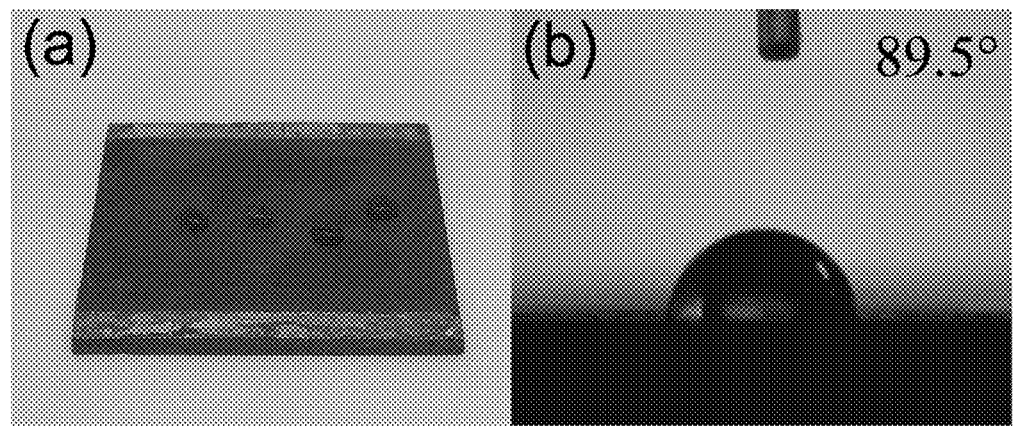
FIG. 5 is digital images of water static contact angle test of electrothermal epoxy composite synthesized in Example 1 of this invention.

By mass, at 50° C., 10 g glycidyl ether type epoxy resin (E51, epoxide equivalent weight of 196 g/eq), 4.2 g of 1,4,5-oxadithiepane-2,7-dione, 4.3 g methylhexahydrophthalic anhydride and 0.05 g 2-ethyl-4-methylimidazole were mixed homogeneously to get prepolymer B; ethyl acetate and 2.07 g unprocessed multi-walled carbon nanotube were added to the prepolymer B, mixed homogeneously, and coated on self-healable epoxy resins prepared in Step (2). After vaporizing ethyl acetate and cured by the protocol of 80° C./2 h, 100° C./2 h, 120° C./2 h, 140° C./2 h and 160° C./4 h, a kind of electrothermal epoxy composites was obtained. The FTIR spectrum, DMA curves and digital images of water static contact angle test of electrothermal epoxy composites are shown in FIG. 3, FIG. 4 and FIG. 5.

4) Synthesis of Modified Superhydrophobic Copper Powders

Figure 6:
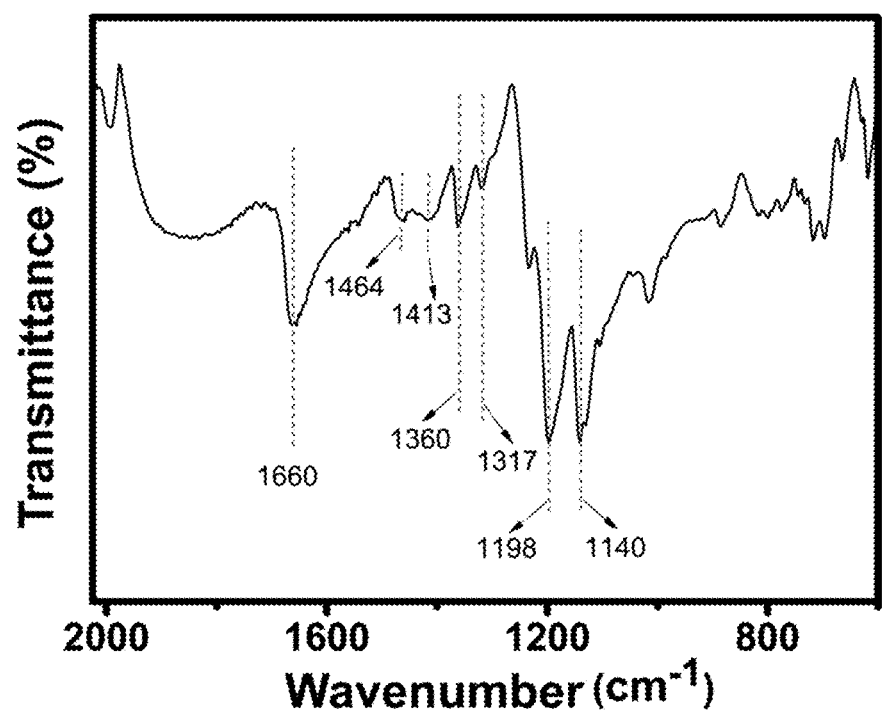
FIG. 6 is FTIR spectrum of modified superhydrophobic copper powders synthesized in Example 1 of this invention.
Figure 7:
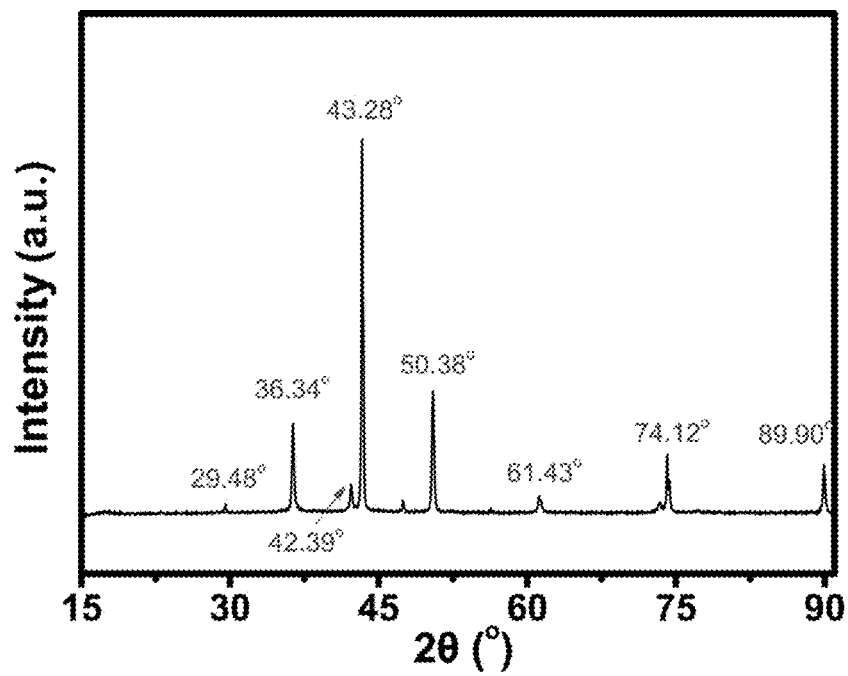
FIG. 7 is XRD pattern of modified superhydrophobic copper powders synthesized in Example 1 of this invention.

By mass, 4 g copper nanopowders and 0.8 g perfluorodecanoic acid were dispersed in water and mixed homogeneously. After filtration and drying, modified superhydrophobic copper powders were obtained. The FTIR spectrum and XRD pattern of modified superhydrophobic copper powders are shown in FIG. 6 and FIG. 7.

5) Synthesis of Superhydrophobic Electrothermal Epoxy Composites

Figure 8:
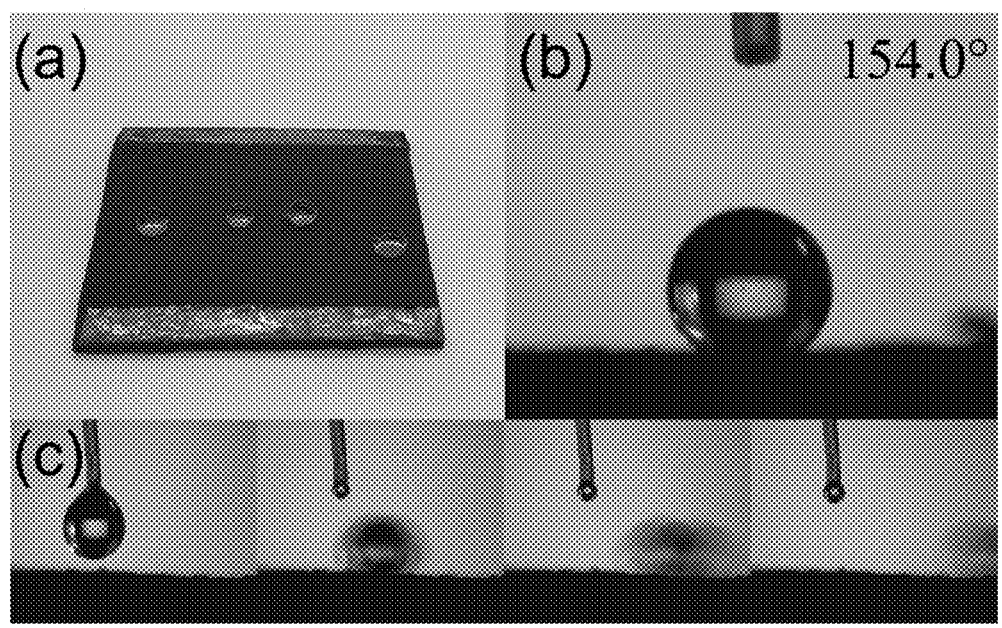
FIG. 8 is digital images of water static contact angle test of superhydrophobic electrothermal epoxy composite synthesized in Example 1 of this invention.
Figure 9:
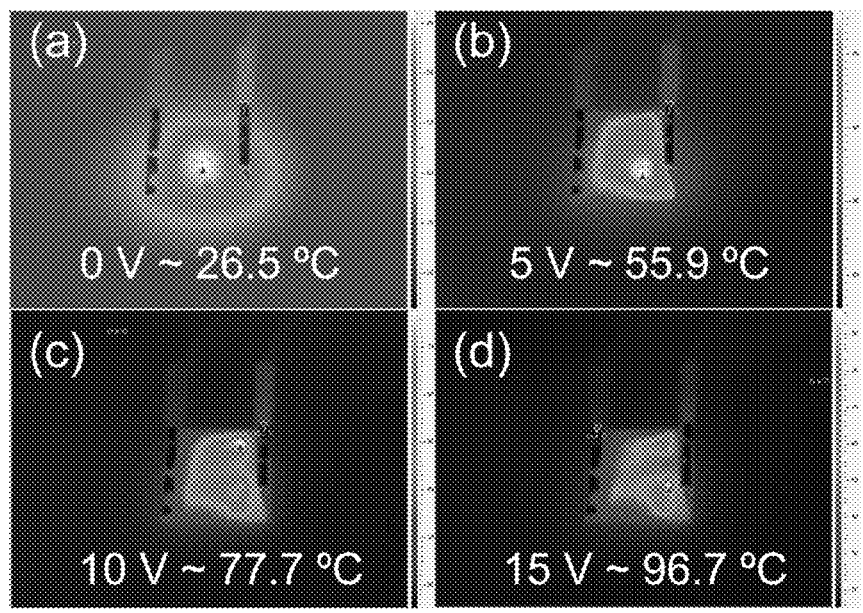
FIG. 9 is near infrared images of superhydrophobic electrothermal epoxy composite synthesized in Example 1 of this invention.
Figure 10:
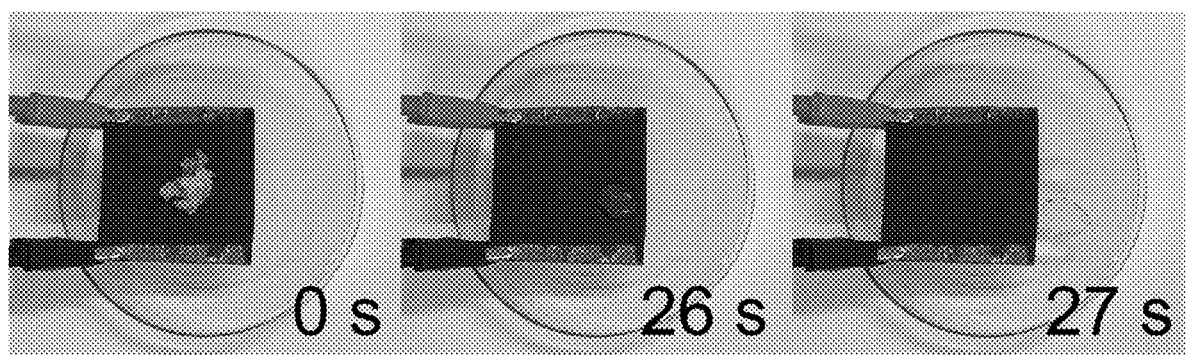
FIG. 10 is digital images of electrothermal ice-removing test of superhydrophobic electrothermal epoxy composite synthesized in Example 1 of this invention.

By mass, at 50° C., 10 g glycidyl ether type epoxy resin (E51, epoxide equivalent weight of 196 g/eq), 4.2 g of 1,4,5-oxadithiepane-2,7-dione, 4.3 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. The digital images of water static contact angle test, near infrared images and digital images of electrothermal ice-removing test of superhydrophobic electrothermal epoxy composites are shown in FIG. 8, FIG. 9 and FIG. 10.

FIG. 1 gives synthetic route of 1,4,5-oxadithiepane-2,7-dione prepared in Example 1. The first step is oxidation reaction of thiols to form dynamic disulfide bonds. The second step is dehydrated condensation of carboxyl groups to form anhydrides that can be cured with epoxides.

FIG. 2 gives $^1$H-NMR spectra of 2,2'-dithiodiacetic acid and 1,4,5-oxadithiepane-2,7-dione prepared in Example 1. Compared with $^1$H-NMR spectra of 2-mercaptoacetic acid, the proton resonating at 2.78 ppm (c) for mercapto groups is not found in the spectrum of 2,2'-dithiodiacetic acid, indicating the formation of disulfides from thiols by oxidative $H_2O_2$. After the dehydrated condensation, no carboxylic protons at 12.75 ppm (b) are observed in spectrum of 1,4,5-oxadithiepane-2,7-dione, proving the formation of anhydrides from carboxyl groups of 2,2'-dithiodiacetic acid.

FIG. 3 gives FTIR spectra of self-healable epoxy resin and electrothermal epoxy composite prepared in Example 1 of this invention. The characteristic vibration between 2800 and 3000 cm$^{-1}$ represent methyl groups (2960 cm$^{-1}$ and 2870 cm$^{-1}$) and methylene groups (2920 cm$^{-1}$ and 2850 cm$^{-1}$). The strong stretching vibration at 1730 cm$^{-1}$ is attributed to carbonyl groups in esters induced by the reaction between epoxides and anhydrides. The appearance of C—S vibration at 1412 cm$^{-1}$ indicates the successful introduction of disulfide groups in the crosslinked network. No obvious asymmetrical stretching vibration peaks assigned to epoxide groups (910 and 845 cm$^{-1}$) are found, so epoxides of self-healable epoxy resin and electrothermal epoxy composite prepared in Example 1 have thoroughly reacted with hardeners.

FIG. 4 gives DMA curves of self-healable epoxy resin and electrothermal epoxy composite prepared in Example 1 of this invention. The peak temperature of tan δ-temperature plot is generally regarded as $T_g$ of thermosetting resins and their derivative composites. For self-healable epoxy resin, a single symmetrical tan δ peak is observed and its $T_g$ is 113° C. In terms of electrothermal epoxy composite, a shoulder peak at 100° C. appears on their tan δ-temperature plots which can be attributed to the intermediate layer between resins and fillers generated by the entanglement among epoxy segments and carbon nanotube. The peak intensity of electrothermal epoxy composite is lower than that of self-healable epoxy resin, suggesting the hindrance effect of carbon nanotube on segmental motion. Note that most self-healable electrothermal materials in exist technical solutions are hydrogels and elastomers, of which $T_g$ values fall in the range from −120 to 20° C., so they are appropriate to be used as sensors and wearable flexible devices. Electrothermal epoxy composite provided in this invention has much better heat-resistance, of which $T_g$ value is 113° C., so it is able to maintain dimensional stability of wind turbine blades when a large amount of electricity transforms into Joule heat for ice removal.

FIG. 5 gives digital images of water static contact angle test of electrothermal epoxy composite prepared in Example 1 of this invention. As shown in FIG. 5a, the water droplets are half-spherical and spread onto the surface of electrothermal epoxy composite with contact angle of 89.5°.

FIG. 6 gives FTIR spectrum of modified superhydrophobic copper powders prepared in Example 1 of this invention. The asymmetrical and symmetrical stretching vibrations of carboxylate anions (—COO$^-$) severally shift toward 1660 cm$^{-1}$ and 1464~1413 cm$^{-1}$ after carboxylic groups are coordinated with Cu. The presence of the bands at 1360 cm$^{-1}$ and 1317 cm$^{-1}$ are attributed to the stretching vibration of —CF$_3$ and those at 1198 cm$^{-1}$ and 1140 cm$^{-1}$ representing characteristic peaks of —CF$_2$, indicating that the surface energy of copper powders is effectively reduced under the modification of perfluorodecanoic acid.

FIG. 8 gives digital images of water static contact angle test of superhydrophobic electrothermal epoxy composite prepared in Example 1 of this invention. After homogeneous adhesion of modified superhydrophobic copper powders on the surface, water droplets on the surface of superhydrophobic electrothermal epoxy composite remain near-spherical (FIG. 8a) and its contact angle increases to 154.0° (FIG. 8b). From snapshots of the sliding angle measurement presented in FIG. 8c, the water droplet is easily rolled off from the surface of superhydrophobic electrothermal epoxy composite with a 3° horizontal tilt. These results have confirmed the superhydrophobicity of superhydrophobic electrothermal epoxy composite provided in this invention.

FIG. 9 gives near infrared images of superhydrophobic electrothermal epoxy composite synthesized in Example 1 of this invention. The balanced heating temperature is adjustable through applying different voltages ranging from 5 to 15 V. According to the Joule effect, it is apparent that the balanced heating temperature grows with higher applied voltage. For instance, when 15 V of voltage is applied between two electrodes along the sides of the sample, the highest balanced temperature could be kept at 96.7° C., which is lower than $T_g$ values (113° C.) of self-healable epoxy resin and electrothermal epoxy composite. Hence, the dimensional stability and service safety of this composite is guaranteed during the process of heat-triggered ice removal.

FIG. 10 gives digital images of electrothermal ice-removing test of superhydrophobic electrothermal epoxy composite synthesized in Example 1 of this invention. The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Example 2

The specific preparation method is composed of following steps: by mass, at 25° C., 120 g 2-mercaptoacetic acid, 600 g methyl acetate and 0.8 g potassium iodide were mixed homogeneously to obtain a solution A; 85 g 30 wt % $H_2O_2$ were added dropwise to solution A and continued to react for 3 h. The obtained solution was washed with 300 mL saturate $Na_2SO_3$ aqueous solution and methyl acetate was removed under reduced pressure to get 2,2'-dithiodiacetic acid.

By mass, at 25° C., 100 g 2,2'-dithiodiacetic acid and 135 g acetic anhydride were mixed homogeneously and continued to react for 3 h. Excess acetic anhydride and generated acetic acid were removed under reduced pressure to get 1,4,5-oxadithiepane-2,7-dione.

By mass, at 60° C., 100 g glycidyl ester type epoxy resin (672, epoxide equivalent weight of 161 g/eq), 65 g of 1,4,5-oxadithiepane-2,7-dione, 15 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 60° C., 10 g glycidyl ester type epoxy resin (672, epoxide equivalent weight of 161 g/eq), 6.5 g of 1,4,5-oxadithiepane-2,7-dione, 1.5 g methylhexahydrophthalic anhydride and 0.05 g 2-ethyl-4-methylimidazole were mixed homogeneously to get prepolymer B; methyl acetate and 1.06 g unprocessed single-walled carbon nanotube were added to the prepolymer B, mixed homogeneously, and coated on self-healable epoxy resins prepared in Step (2). After vaporizing methyl acetate and cured by the protocol of 80° C./2 h, 100° C./2 h, 120° C./2 h, 140° C./2 h and 160° C./4 h, a kind of electrothermal epoxy composites with $T_g$ above 110° C. was obtained. $T_g$ was over 110° C.

By mass, 4 g copper nanopowders and 0.1 g perfluorooctanoic acid were dispersed in water and mixed homogeneously. After filtration and drying, modified superhydrophobic copper powders were obtained.

By mass, at 60° C., 10 g glycidyl ester type epoxy resin (672, epoxide equivalent weight of 161 g/eq), 6.5 g of 1,4,5-oxadithiepane-2,7-dione, 1.5 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Fractured surfaces of damaged superhydrophobic electrothermal epoxy composites were brought into contact, held tightly by clamps and maintained at 180° C. for 2 h to fulfill their self-healing process. The healed samples fuse together as entirety and still exhibit excellent superhydrophobicity.

Example 3

The specific preparation method is composed of following steps: by mass, at 30° C., 120 g 2-mercaptoacetic acid, 700 g propyl acetate and 1.0 g potassium iodide were mixed homogeneously to obtain a solution A; 90 g 30 wt % $H_2O_2$ were added dropwise to solution A and continued to react for 4 h. The obtained solution was washed with 300 mL saturate $Na_2SO_3$ aqueous solution and propyl acetate was removed under reduced pressure to get 2,2'-dithiodiacetic acid.

By mass, at 30° C., 100 g 2,2'-dithiodiacetic acid and 120 g acetic anhydride were mixed homogeneously and continued to react for 4 h. Excess acetic anhydride and generated acetic acid were removed under reduced pressure to get 1,4,5-oxadithiepane-2,7-dione.

By mass, at 70° C., 100 g glycidyl amine type epoxy resin (AFG-90, epoxide equivalent weight of 118 g/eq), 55 g of 1,4,5-oxadithiepane-2,7-dione, 25 g methylhexahydrophthalic anhydride and 0.5 g 2-ethyl-4-methylimidazole were mixed homogeneously. After cured by the protocol of 80°

C./2 h, 100° C./2 h, 120° C./2 h, 140° C./2 h and 160° C./4 h, a kind of self-healable epoxy resins was obtained.

By mass, at 70° C., 10 g glycidyl amine type epoxy resin (AFG-90, epoxide equivalent weight of 118 g/eq), 5.5 g of 1,4,5-oxadithiepane-2,7-dione, 2.5 g methylhexahydrophthalic anhydride and 0.05 g 2-ethyl-4-methylimidazole were mixed homogeneously to get prepolymer B; methyl propionate, 1.04 g unprocessed single-walled carbon nanotube and 1.04 g unprocessed multi-walled carbon nanotube were added to the prepolymer B, mixed homogeneously, and coated on self-healable epoxy resins prepared in Step (2). After vaporizing methyl propionate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders and 2.1 g perfluorononanoic acid were dispersed in water and mixed homogeneously. After filtration and drying, modified superhydrophobic copper powders were obtained.

By mass, at 50° C., 10 g glycidyl amine type epoxy resin (AFG-90, epoxide equivalent weight of 118 g/eq), 5.5 g of 1,4,5-oxadithiepane-2,7-dione, 2.5 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Fractured surfaces of damaged superhydrophobic electrothermal epoxy composites were brought into contact, held tightly by clamps and maintained at 200° C. for 3 h to fulfill their self-healing process. The healed samples fuse together as entirety and still exhibit excellent superhydrophobicity.

Example 4

The specific preparation method is composed of following steps: by mass, at 25° C., 120 g 2-mercaptoacetic acid, 500 g methyl propionate and 1.2 g potassium iodide were mixed homogeneously to obtain a solution A; 85 g 30 wt % $H_2O_2$ were added dropwise to solution A and continued to react for 2.5 h. The obtained solution was washed with 300 mL saturate $Na_2SO_3$ aqueous solution and methyl propionate was removed under reduced pressure to get 2,2'-dithiodiacetic acid.

By mass, at 25° C., 100 g 2,2'-dithiodiacetic acid, 75 g acetic anhydride and 75 g trifluoroacetic anhydride were mixed homogeneously and continued to react for 2.5 h. Excess anhydride and generated carboxylic acid were removed under reduced pressure to get 1,4,5-oxadithiepane-2,7-dione.

By mass, at 70° C., 100 g aliphatic epoxides (EPG-205, epoxide equivalent weight of 178 g/eq), 44 g of 1,4,5-oxadithiepane-2,7-dione, 41 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 70° C., 10 g aliphatic epoxides (EPG-205, epoxide equivalent weight of 178 g/eq), 4.4 g of 1,4,5-oxadithiepane-2,7-dione, 4.1 g methylhexahydrophthalic anhydride and 0.05 g 2-ethyl-4-methylimidazole were mixed homogeneously to get prepolymer B; ethyl propionate and 2.01 g unprocessed multi-walled carbon nanotube were added to the prepolymer B, mixed homogeneously, and coated on self-healable epoxy resins prepared in Step (2). After vaporizing ethyl propionate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders, 0.8 g perfluorodecanoic acid and 0.8 g perfluorooctanoic acid were dispersed in water and mixed homogeneously. After filtration and drying, modified superhydrophobic copper powders were obtained.

By mass, at 70° C., 10 g aliphatic epoxides (EPG-205, epoxide equivalent weight of 178 g/eq), 4.4 g of 1,4,5-oxadithiepane-2,7-dione, 4.1 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Self-Healing Method of Superhydrophobic Electrothermal Epoxy Composites

Fractured surfaces of damaged superhydrophobic electrothermal epoxy composites were brought into contact, held tightly by clamps and maintained at 160° C. for 2 h to fulfill their self-healing process. The healed samples fuse together as entirety and still exhibit excellent superhydrophobicity.

Example 5

The specific preparation method is composed of following steps: by mass, at 25° C., 120 g 2-mercaptoacetic acid, 600 g ethyl propionate and 0.7 g potassium iodide were mixed homogeneously to obtain a solution A; 85 g 30 wt % $H_2O_2$ were added dropwise to solution A and continued to react for 2 h. The obtained solution was washed with 300 mL saturate $Na_2SO_3$ aqueous solution and ethyl propionate was removed under reduced pressure to get 2,2'-dithiodiacetic acid.

By mass, at 25° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

By mass, at 50° C., 100 g alicyclic epoxides (H71, epoxide equivalent weight of 154 g/eq), 51 g of 1,4,5-oxadithiepane-2,7-dione, 34 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 50° C., 10 g alicyclic epoxides (H71, epoxide equivalent weight of 154 g/eq), 5.1 g of 1,4,5-oxadithiepane-2,7-dione, 3.4 g methylhexahydrophthalic anhydride and 0.05 g 2-ethyl-4-methylimidazole were mixed homogeneously to get prepolymer B; ethyl acetate, methyl acetate and 1.09 g unprocessed single-walled carbon nanotube were added to the prepolymer B, mixed homogeneously, and coated on self-healable epoxy resins prepared in Step (2). After vaporizing ethyl acetate, methyl acetate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders, 0.8 g perfluorodecanoic acid and 1.0 g perfluorononanoic acid were dispersed in water and mixed homogeneously. After filtration and drying, modified superhydrophobic copper powders were obtained.

By mass, at 50° C., 10 g alicyclic epoxides (H71, epoxide equivalent weight of 154 g/eq), 5.1 g of 1,4,5-oxadithiepane-2,7-dione, 3.4 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Self-Healing Method of Superhydrophobic Electrothermal Epoxy Composites

Fractured surfaces of damaged superhydrophobic electrothermal epoxy composites were brought into contact, held tightly by clamps and maintained at 175° C. for 1 h to fulfill their self-healing process. The healed samples fuse together as entirety and still exhibit excellent superhydrophobicity.

Example 6

The specific preparation method is composed of following steps: by mass, at 23° C., 120 g 2-mercaptoacetic acid, 250 g ethyl acetate, 250 g propyl acetate and 0.6 g potassium iodide were mixed homogeneously to obtain a solution A; 83 g 30 wt % $H_2O_2$ were added dropwise to solution A and continued to react for 3 h. The obtained solution was washed with 300 mL saturate $Na_2SO_3$ aqueous solution and ethyl acetate and propyl acetate were removed under reduced pressure to get 2,2'-dithiodiacetic acid.

By mass, at 23° C., 100 g 2,2'-dithiodiacetic acid and 140 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

By mass, at 50° C., 50 g glycidyl ether type epoxy resin (E51, epoxide equivalent weight of 196 g/eq), 50 g glycidyl ester type epoxy resin (672, epoxide equivalent weight of 161 g/eq), 44 g of 1,4,5-oxadithiepane-2,7-dione, 41 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 50° C., 5 g glycidyl ether type epoxy resin (E51, epoxide equivalent weight of 196 g/eq), 5 g glycidyl ester type epoxy resin (672, epoxide equivalent weight of 161 g/eq), 4.4 g of 1,4,5-oxadithiepane-2,7-dione, 4.1 g methylhexahydrophthalic anhydride and 0.05 g 2-ethyl-4-methylimidazole were mixed homogeneously to get prepolymer B; methyl acetate, methyl propionate and 1.17 g unprocessed multi-walled carbon nanotube were added to the prepolymer B, mixed homogeneously, and coated on self-healable epoxy resins prepared in Step (2). After vaporizing methyl acetate, methyl propionate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders, 0.6 g perfluorooctanoic acid and 0.2 g perfluorononanoic acid were dispersed in water and mixed homogeneously. After filtration and drying, modified superhydrophobic copper powders were obtained.

By mass, at 50° C., 5 g glycidyl ether type epoxy resin (E51, epoxide equivalent weight of 196 g/eq), 5 g glycidyl ester type epoxy resin (672, epoxide equivalent weight of 161 g/eq), 4.4 g of 1,4,5-oxadithiepane-2,7-dione, 4.1 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Self-Healing Method of Superhydrophobic Electrothermal Epoxy Composites

Fractured surfaces of damaged superhydrophobic electrothermal epoxy composites were brought into contact, held tightly by clamps and maintained at 180° C. for 3 h to fulfill their self-healing process. The healed samples fuse together as entirety and still exhibit excellent superhydrophobicity.

Example 7

The specific preparation method is composed of following steps: by mass, at 25° C., 120 g 2-mercaptoacetic acid, 250 g methyl acetate, 350 g methyl propionate and 1.1 g potassium iodide were mixed homogeneously to obtain a solution A; 84 g 30 wt % $H_2O_2$ were added dropwise to solution A and continued to react for 2 h. The obtained solution was washed with 300 mL saturate $Na_2SO_3$ aqueous solution and methyl acetate and methyl propionate was removed under reduced pressure to get 2,2'-dithiodiacetic acid.

By mass, at 22° C., 100 g 2,2'-dithiodiacetic acid and 150 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

By mass, at 50° C., 40 g alicyclic epoxides (H71, epoxide equivalent weight of 154 g/eq), 60 g glycidyl ester type epoxy resin (672, epoxide equivalent weight of 161 g/eq), 44 g of 1,4,5-oxadithiepane-2,7-dione, 30 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 50° C., 4 g alicyclic epoxides (H71, epoxide equivalent weight of 154 g/eq), 6 g glycidyl ester type epoxy resin (672, epoxide equivalent weight of 161 g/eq), 4.4 g of 1,4,5-oxadithiepane-2,7-dione, 3 g methylhexahydrophthalic anhydride and 0.05 g 2-ethyl-4-methylimidazole were mixed homogeneously to get prepolymer B; methyl propionate, ethyl propionate and 1.72 g unprocessed single-walled carbon nanotube were added to the prepolymer B, mixed homogeneously, and coated on self-healable epoxy resins prepared in Step (2). After vaporizing methyl propionate, ethyl propionate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders and 0.8 g perfluorodecanoic acid were dispersed in water and mixed homogeneously. After filtration and drying, modified superhydrophobic copper powders were obtained.

By mass, at 50° C., 4 g alicyclic epoxides (H71, epoxide equivalent weight of 154 g/eq), 6 g glycidyl ester type epoxy resin (672, epoxide equivalent weight of 161 g/eq), 4.4 g of 1,4,5-oxadithiepane-2,7-dione, 3 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Self-Healing Method of Superhydrophobic Electrothermal Epoxy Composites

Fractured surfaces of damaged superhydrophobic electrothermal epoxy composites were brought into contact, held tightly by clamps and maintained at 185° C. for 1.5 h to fulfill their self-healing process. The healed samples fuse together as entirety and still exhibit excellent superhydrophobicity.

Example 8

The specific preparation method is composed of following steps: by mass, at 25° C., 120 g 2-mercaptoacetic acid, 300 g ethyl acetate, 300 g ethyl propionate and 1.0 g potassium iodide were mixed homogeneously to obtain a solution A; 85 g 30 wt % $H_2O_2$ were added dropwise to solution A and continued to react for 2.5 h. The obtained solution was washed with 300 mL saturate $Na_2SO_3$ aqueous solution and ethyl acetate and ethyl propionate was removed under reduced pressure to get 2,2'-dithiodiacetic acid.

By mass, at 24° C., 100 g 2,2'-dithiodiacetic acid and 135 g trifluoroacetic anhydride were mixed homogeneously and continued to react for 2 h. Excess trifluoroacetic anhydride and generated trifluoroacetic acid were removed under reduced pressure to get 1,4,5-oxadithiepane-2,7-dione.

By mass, at 50° C., 70 g alicyclic epoxides (H71, epoxide equivalent weight of 154 g/eq), 30 g glycidyl ether type epoxy resin (E51, epoxide equivalent weight of 196 g/eq), 52 g of 1,4,5-oxadithiepane-2,7-dione, 31 g methylhexahydrophthalic anhydride and 0.5 g 2-ethyl-4-methylimidazole were mixed homogeneously. After cured by the protocol of 80° C./2 h, 100° C./2 h, 120° C./2 h, 140° C./2 h and 160° C./4 h, a kind of self-healable epoxy resins was obtained.

By mass, at 50° C., 7 g alicyclic epoxides (H71, epoxide equivalent weight of 154 g/eq), 3 g glycidyl ether type epoxy resin (E51, epoxide equivalent weight of 196 g/eq), 5.2 g of 1,4,5-oxadithiepane-2,7-dione, 3.1 g methylhexahydrophthalic anhydride and 0.05 g 2-ethyl-4-methylimidazole were mixed homogeneously to get prepolymer B; methyl acetate and 2.84 g unprocessed multi-walled carbon nanotube were added to the prepolymer B, mixed homogeneously, and coated on self-healable epoxy resins prepared in Step (2). After vaporizing methyl acetate and cured by the protocol of 80° C./2 h, 100° C./2 h, 120° C./2 h, 140° C./2 h and 160° C./4 h, a kind of electrothermal epoxy composites with $T_g$ above 110° C. was obtained.

By mass, 4 g copper nanopowders and 0.8 g perfluorodecanoic acid were dispersed in water and mixed homogeneously. After filtration and drying, modified superhydrophobic copper powders were obtained.

By mass, at 50° C., 7 g alicyclic epoxides (H71, epoxide equivalent weight of 154 g/eq), 3 g glycidyl ether type epoxy resin (E51, epoxide equivalent weight of 196 g/eq), 5.2 g of 1,4,5-oxadithiepane-2,7-dione, 3.1 g methylhexahydrophthalic anhydride and 0.05 g 2-ethyl-4-methylimidazole were mixed homogeneously to get prepolymer C. The prepolymer C was coated on the electrothermal epoxy composites prepared in Step (3) and then modified superhydrophobic copper powders were dispersed on prepolymer C. After cured by the protocol of 80° C./2 h, 100° C./2 h, 120° C./2 h, 140° C./2 h and 160° C./4 h, a kind of superhydrophobic electrothermal epoxy composites was obtained. Water droplets are half-spherical and spread onto the surface of electrothermal epoxy composite, indicating good superhydrophobicity of superhydrophobic electrothermal epoxy composite like lotus leaf.

The composite was held nearly horizontal with 3° tilt and a voltage of 10 V was applied along the sides of the sample to start transducing electrical energy into Joule heating energy. An ice block was placed on the surface, which was completely melt within 26 s, and then the resulting water droplet rolled off from the superhydrophobic surface, and no water residue was left. This experiment clearly demonstrates that a combination of good superhydrophobicity and electrothermal feature bestows superhydrophobic electrothermal epoxy composite provided in this invention with a unique ice-removing ability which meets the urgent demand of wind turbine blades.

Self-Healing Method of Superhydrophobic Electrothermal Epoxy Composites

Fractured surfaces of damaged superhydrophobic electrothermal epoxy composites were brought into contact, held tightly by clamps and maintained at 175° C. for 1.3 h to fulfill their self-healing process. The healed samples fuse together as entirety and still exhibit excellent superhydrophobicity.

Example 9 Self-Healing Method of Superhydrophobic Electrothermal Epoxy Composites Fractured surfaces of damaged superhydrophobic electrothermal epoxy composites prepared in Example 1 were brought into contact, held tightly by clamps and maintained at 160° C. for 1 h to fulfill their self-healing process. The digital images of self-healing process and water static contact angle test of healed superhydrophobic electrothermal epoxy composite are shown in FIG. 11 and FIG. 12.

Figure 11:
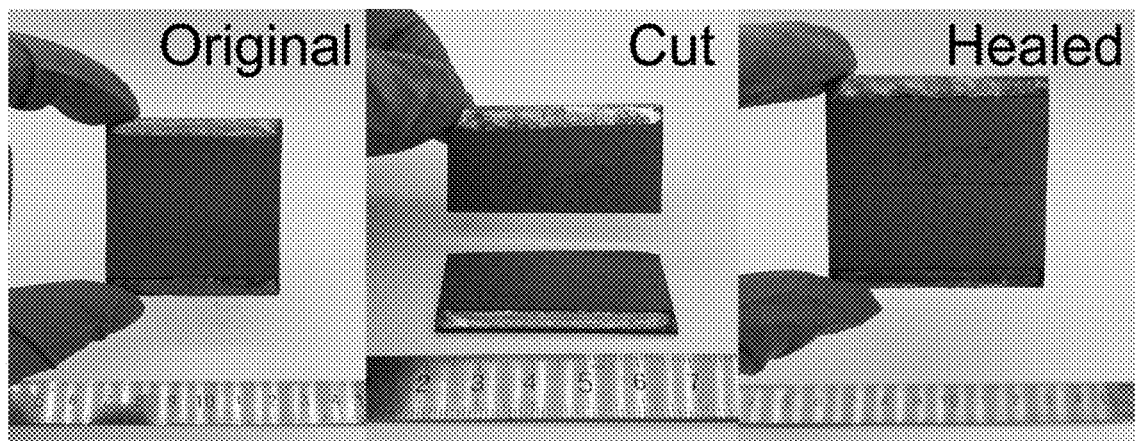
FIG. 11 is digital images of self-healing process of superhydrophobic electrothermal epoxy composite synthesized in Example 9 of this invention.

FIG. 11 gives digital images of self-healing process of superhydrophobic electrothermal epoxy composite prepared in Example 1 of this invention. An intact composite was thoroughly cut into two pieces in the middle of the sample; the two pieces of samples were contacted at the fractured surface and then held tightly by clamps. After maintained at 160° C. for 1 h in the blast oven, the two pieces fused together and became an entire sample with a scar on the surface through topology rearrangement of resin layers containing dynamic disulfide bonds.

Figure 12:
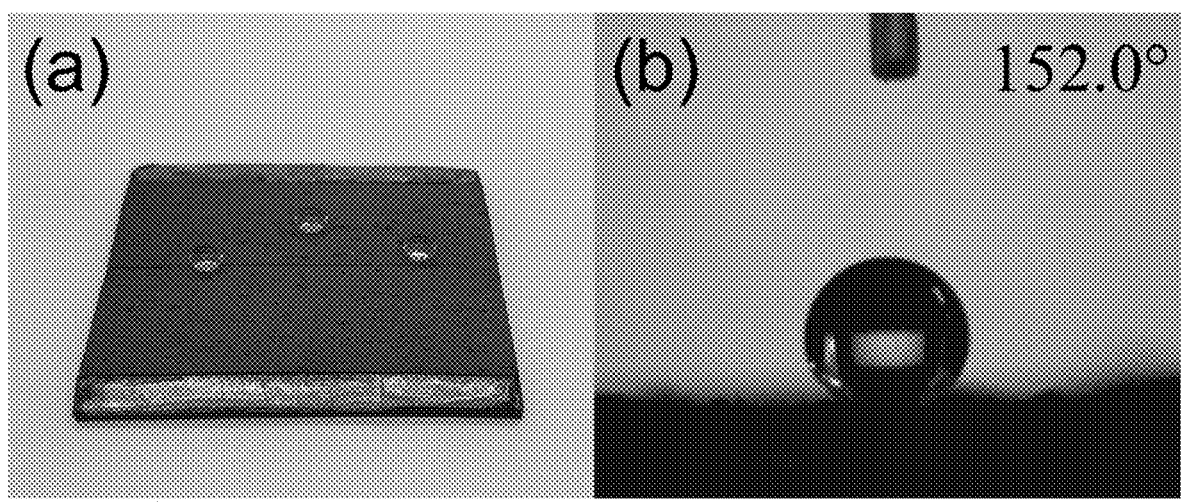
FIG. 12 is digital images of water static contact angle test of healed superhydrophobic electrothermal epoxy composite synthesized in Example 9 of this invention.

FIG. 12 gives digital images of water static contact angle test of healed superhydrophobic electrothermal epoxy composite prepared in Example 1 of this invention. Water droplets remain nearly spherical on the surface. Especially, the shape of the water droplet staying on the scar after self-healing is identical to others with static water contact angle as high as 152.0°. Hence, the self-healing process does not change the surface wettability and the superhydrophobicity is successfully reserved.

In this invention, 1,4,5-oxadithiepane-2,7-dione and methylhexahydrophthalic anhydride were mixed and cured with epoxides to get self-healable epoxy resins; carbon nanotube/self-healable epoxy resin prepolymers were coated on self-healable epoxy resins and cured to get electrothermal epoxy composites; modified superhydrophobic copper powders were adhered on electrothermal epoxy composites and cured to get a kind of superhydrophobic electrothermal epoxy composites. Through the topology rearrangement based on exchange of dynamic disulfide bonds, fast self-healing process is achieved in self-healable epoxy resin, electrothermal lyer and superhydrophobic layer. The thermal resistance of superhydrophobic electrothermal epoxy composites is superior to existed technical solutions and they can simultaneously repair cracking and delamination and the healed samples still exhibit excellent superhydrophobicity. These merits of superhydrophobic electrothermal epoxy composites provided in this invention can meet the harsh requirements of self-healing and removing ice on surfaces of wind turbine blades, suggesting good abilities of guaranteeing service safety and lifespan of wind turbine blades.

The invention claimed is:

1. A method of preparing superhydrophobic electrothermal epoxy composites, comprising:
   (1) mixing 100 parts of an epoxy resin, 42 to 84 parts of 1,4,5-oxadithiepane-2,7-dione and 0 to 43 parts of methylhexahydrophthalic anhydride, by weight, homogeneously at 50 to 70° C., and curing to obtain self-healable epoxy resins;
   (2) mixing 10 parts of the epoxy resin, 4.2 to 8.4 parts of 1,4,5-oxadithiepane-2,7-dione, and 0 to 4.3 parts of methylhexahydrophthalic anhydride, by weight, homogeneously at 50 to 70° C. to obtain a first prepolymer, adding 0.1 to 4 parts of a carbon nanotube by weight and an ester solvent to the first prepolymer and mixing homogeneously to obtain a paste, coating the self-healable epoxy resins obtained in the step (1) with the paste, evaporating the ester solvent and curing to obtain electrothermal epoxy composites;
   (3) dispersing 4 parts of copper nanopowders and 0.1 to 2 parts of perfluorocarboxylic acid, by weight, in water, mixing homogeneously, filtering and drying to obtain modified superhydrophobic copper powders;
   (4) mixing at 50 to 70° C., 10 parts of epoxy resin, 4.2 to 8.4 parts of 1,4,5-oxadithiepane-2,7-dione and 0 to 4.3 parts of methylhexahydrophthalic anhydride, by weight, homogeneously to obtain a second prepolymer, dispersing the second prepolymer and the modified superhydrophobic copper powders sequentially on the electrothermal epoxy composites obtained in the step (2), and curing to obtain the superhydrophobic electrothermal epoxy composites.

2. The method according to claim 1, wherein the 1,4,5-oxadithiepane-2,7-dione is prepared by a method comprising:
   (1) mixing 120 parts of 2-mercaptoacetic acid, 500 to 700 parts of the ester solvent and 0.6 to 1.2 parts of potassium iodide, by weight, homogeneously at 20 to 30° C. to obtain a solution, adding 80 to 90 parts of 30 wt % $H_2O_2$, by weight, dropwise to the solution, and continuing to react for 2 to 4 hour to get 2,2'-dithiodiacetic acid;
   (2) mixing 100 parts of 2,2'-dithiodiacetic acid and 120 to 150 parts of an acid anhydride, by weight, homogeneously at 20 to 30° C., and continuing to react for 2 to 4 hours to obtain the 1,4,5-oxadithiepane-2,7-dione.

3. The method according to claim 2, wherein the acid anhydride is selected from the group consisting of acetic anhydride, trifluoroacetic anhydride, and a combination thereof.

4. The method according to claim 1, wherein the ester solvent is selected from the group consisting of methyl acetate, ethyl acetate, propyl acetate, methyl propionate, ethyl propionate, and a combination thereof.

5. The method according to claim 1, wherein the perfluorocarboxylic acid is selected from the group consisting of perfluorooctanoic acid, perfluorononanoic acid, perfluorodecanoic acid, and a combination thereof.

6. The method according to claim 1, wherein the epoxy resin is selected from the group consisting of a glycidyl ether type epoxy resin, a glycidyl ester type epoxy resin, a glycidyl amine type epoxy resin, aliphatic epoxides, alicyclic epoxides, and a combination thereof.

7. The method according to claim 1, wherein the carbon nanotube is selected from the group consisting of an unprocessed single-walled carbon nanotube, a multi-walled carbon nanotube, and a combination thereof.

8. The method according to claim 1, further comprising:
heating the superhydrophobic electrothermal epoxy composites at 160 to 200° C. for 1 to 3 hours to complete a self-healing process.

* * * * *